(12) United States Patent
Zhang et al.

(10) Patent No.: US 11,733,121 B2
(45) Date of Patent: Aug. 22, 2023

(54) SEALING INTEGRITY EVALUATION DEVICE FOR HIGH-TEMPERATURE AND HIGH- PRESSURE CASING-CEMENT RING-FORMATION AND METHOD THEREOF

(71) Applicants: Southwest Petroleum University, Sichuan (CN); Engineering Technology Research Institute, Southwest Oil and Gas Field Company of Petro China, Sichuan (CN)

(72) Inventors: Zhi Zhang, Sichuan (CN); Duo Hou, Sichuan (CN); Huali Zhang, Sichuan (CN); Yufei Li, Sichuan (CN); You Wu, Sichuan (CN); Lin Zhang, Sichuan (CN); Wei Luo, Sichuan (CN); Chuanlei Wang, Sichuan (CN); Xiankang Zhong, Sichuan (CN); Pengfei Sang, Sichuan (CN)

(73) Assignees: Southwest Petroleum University, Sichuan (CN); Engineering Technology Research Institute, Southwest Oil and Gas FieldCompany of Petro China, Sichuan (CN)

( * ) Notice: Subject to any disclaimer, the term of this patent is extended or adjusted under 35 U.S.C. 154(b) by 262 days.

(21) Appl. No.: 17/229,802

(22) Filed: Apr. 13, 2021

(65) Prior Publication Data
US 2021/0231520 A1    Jul. 29, 2021

(30) Foreign Application Priority Data
Aug. 26, 2020    (CN) .......................... 202010867022.3

(51) Int. Cl.
G01M 3/02    (2006.01)
G01M 3/26    (2006.01)
(Continued)

(52) U.S. Cl.
CPC ................ *G01M 3/26* (2013.01); *G01M 3/06* (2013.01); *G01N 21/95* (2013.01); *G01N 23/046* (2013.01);
(Continued)

(58) Field of Classification Search
CPC . G01M 3/06; G01M 3/26; G01N 3/12; G01N 3/18; G01N 21/95; G01N 23/046;
(Continued)

(56) References Cited

U.S. PATENT DOCUMENTS 4,421,169 A      12/1983  Dearth et al.
4,425,810 A  *   1/1984   Simon .................... G01N 23/06
                                                             374/45
(Continued)

FOREIGN PATENT DOCUMENTS

CN            104406910 A       3/2015
CN         201410572060         3/2015
(Continued)

*Primary Examiner* — Alexander A Mercado

(57) ABSTRACT

A sealing integrity evaluation device for high-temperature and high-pressure casing-cement ring-formation and a method thereof are provided. the device includes: a high-temperature autoclave, a temperature and pressure control system, and a casing-cement-formation combination; wherein the autoclave realizes alternating temperature and pressure during the experiment; the control system monitors, controls and records the temperature and pressure data; the combination simulates a full size or a compact size casing-cement-formation of a well. Casing-cement-formation combination samples are designed and prepared by simulating working conditions such as alternating temperature, pressure, and casing internal pressure, by testing the channeling and leakage pressure of the first interface and the second interface of combination, analyzing the shape and size of the internal defects, testing the compressive strength, provided a more stable and reliable experimental method and data (Continued)

support for the detection of cementing sheath sealing ability and the evaluation of sealing integrity.

4 Claims, 3 Drawing Sheets

(51) Int. Cl.
    *G01M 3/06*       (2006.01)
    *G01N 21/95*     (2006.01)
    *G01N 23/046*    (2018.01)
    *G01N 23/06*     (2018.01)
    *G01N 33/38*     (2006.01)
    *E21B 33/14*     (2006.01)

(52) U.S. Cl.
    CPC ........... *G01N 23/06* (2013.01); *G01N 33/383* (2013.01); *E21B 33/14* (2013.01); *G01N 2223/04* (2013.01); *G01N 2223/419* (2013.01); *G01N 2223/646* (2013.01)

(58) Field of Classification Search
    CPC ............... G01N 23/06; G01N 2223/04; G01N 2223/419; G01N 2203/0232; G01N 33/383; E21B 33/14; E21B 49/00
    See application file for complete search history.

(56) References Cited

U.S. PATENT DOCUMENTS

| | | | | |
|---|---|---|---|---|
| 6,112,599 | A * | 9/2000 | Maki, Jr. ................ | G01N 29/30 73/587 |
| 2007/0056383 | A1 * | 3/2007 | Deeg ................... | G01N 33/383 73/788 |
| 2007/0137285 | A1 * | 6/2007 | Jennings ................ | G01F 22/00 73/149 |
| 2008/0168848 | A1 * | 7/2008 | Funkhouser ............. | G01N 3/10 73/865.6 |
| 2008/0178683 | A1 * | 7/2008 | Heathman ................ | G01N 3/24 73/803 |
| 2009/0084189 | A1 * | 4/2009 | McMechan ............... | G01N 3/12 73/803 |
| 2011/0094295 | A1 * | 4/2011 | Meadows ................ | G01N 3/08 73/38 |
| 2014/0007695 | A1 * | 1/2014 | Darbe ..................... | G01N 3/12 73/803 |
| 2017/0121587 | A1 * | 5/2017 | Allouche ................ | C04B 28/04 |
| 2017/0205388 | A1 * | 7/2017 | Thomas ................ | E21B 47/005 |
| 2019/0302092 | A1 * | 10/2019 | Wang ................... | E21B 47/005 |
| 2021/0048381 | A1 * | 2/2021 | Gamwell ................ | G01N 3/02 |
| 2021/0356452 | A1 * | 11/2021 | Musso ..................... | G01N 3/12 |

FOREIGN PATENT DOCUMENTS

| | | |
|---|---|---|
| CN | 106522923 | 3/2017 |
| CN | 104500034 | 4/2017 |
| CN | 107167396 | 9/2017 |
| CN | 108358483 A | 8/2018 |
| CN | 108361024 A | 8/2018 |
| CN | 201910171718 | 4/2019 |
| CN | 2019109305084 | 12/2019 |
| CN | 210105843 | 2/2020 |
| WO | 2020016169 | 1/2020 |
| WO | 2020027834 | 2/2020 |
| WO | 2020076180 | 4/2020 |
| WO | 2014100269 | 6/2020 |

* cited by examiner

SEALING INTEGRITY EVALUATION DEVICE FOR HIGH-TEMPERATURE AND HIGH- PRESSURE CASING-CEMENT RING-FORMATION AND METHOD THEREOF

CROSS REFERENCE OF RELATED APPLICATION

The present invention claims priority under 35 U.S.C. 119(a-d) to CN 202010867022.3, filed Aug. 26, 2020.

BACKGROUND OF THE PRESENT INVENTION

Field of Invention

The present invention relates to a technical field of mining, and more particularly to a method for evaluating sealing integrity of a casing/cement ring/formation combination in a cementing process of a high-temperature and high-pressure oil and gas well, and also to a device which uses the method for evaluating sealing integrity of a casing/cement ring/formation combination of a high-temperature and high-pressure oil and gas well.

Description of Related Arts

Energy is an important material foundation and source of power for economic and social development. The sustained development of the world economy has even higher requirements for energy. Cementing engineering is an important link to ensure safe and efficient development of oil and gas. Cementing quality is the key to isolating oil, gas and water layers in the wellbore, protecting oil and gas well casings, prolonging the life of oil and gas wells, improving oil recovery, and developing oil and gas resources scientifically and rationally. With the continuous increase in oil and gas exploration and development efforts, cementing technology is facing ultra-deep, ultra-high temperature and ultra-high pressure, complex reservoirs and complex geological conditions. The impact of high temperature and high pressure on the displacement efficiency of cement slurry and the strength of interfacial cementation, the impact of annular air channeling and pressure leakage formations on the permeability and compressive strength of the cement ring, and the synergistic effect of $CO_2$, $H_2S$ and other corrosive gases with formation water all lead to changes in the mechanical properties and related physical properties of the cement ring, which can easily cause sealing integrity failure of the casing/cement ring/formation, leading to huge risks to service life of the oil and gas wells, wellbore integrity, personnel safety and economic benefits.

The cementing process refers to the injection of cement slurry on the ground through the casing string into the annulus between the wellbore and the casing string. As the cement solidifies, a cement ring is formed and the casing string and the well wall rock are firmly fixed together. The stress and deformation of the casing string and the in-situ stress of the formation rock are all directly applied on the cement ring. The cement ring is also affected by the pressure of the external liquid column. Therefore, the analysis and evaluation of channeling detection, leakage property, cement stone mechanical properties and internal defects of the casing/cement ring/formation combination are important basis for selecting and evaluating cement slurry systems for the high-temperature and high-pressure oil and gas wells.

In summary, the sealing integrity evaluation of the casing/cement ring/formation combination of the high-temperature and high-pressure oil and gas wells is extremely important in theory and engineering. However, due to the lack of scientific and reasonable evaluation devices and methods close to the site, the performance evaluation results of the cement slurry system deviate from the actual engineering, which seriously affects the quality improvement of the high-temperature and high-pressure oil and gas well cementing and the development of wellbore integrity.

The conventional cement ring integrity evaluation method uses the simulated casing sample to form the first cementing interface with the cement ring, so as to evaluate sealing ability and sealing performance of the first cementing interface; or uses rubber materials to simulate formation rocks to realize the evaluation of cement ring seal failure performance under certain confining pressure. However, the simulation evaluation results are far from the actual oil and gas well engineering. The evaluation device has a complex structure, large volume, high cost, which is not conducive to miniaturized low-cost indoor experiments and failure mechanism research of cement ring sealing. When using the conventional methods to select and evaluate suitability of the cement slurry system required for the ultra-deep, ultra-high-temperature and ultra-high-pressure wellbores, it is impossible to simulate the second cementing interface formed by the cement ring and the formation, alternating temperature pressure, internal pressure, confining pressure, and other factors. Therefore, the evaluation environment is inconsistent with the site due to the comprehensive effects, making the evaluation results unsuitable for site conditions. That is to say, the cement slurry system cementing quality is poor, resulting in huge economic losses during the operation of high-temperature and high-pressure oil and gas wells and even causing wellbore integrity risks.

Conventionally, the casing/cement ring/formation sealing integrity evaluation methods have the following shortcomings:

(A) The solidification method of the casing/cement ring/formation rock is limited, which cannot precisely simulate the first cementing interface, the second cementing interface, as well as the alternating high temperature, internal pressure, confining pressure, and medium complex working conditions.

(B) Sample structure, material and experimental conditions of the casing/cement ring/formation combination are different from the actual high-temperature and high-pressure oil and gas well engineering, which cannot provide reliable guarantee for the optimization and applicability evaluation of the on-site cement slurry system;

(C) The cementing condition and sealing ability of the first cementing interface between the casing and the cement ring and the second cementing interface between the cement ring and the formation rock cannot be detected at the same time, so it is impossible to truly evaluate the sealing integrity of the casing/cement ring/formation combination in the ultra-deep, ultra-high temperature and ultra-high pressure environment.

In order to solve the problem that the conventional sealing integrity evaluation method for casing/cement ring/formation combination cannot select a cement slurry system suitable for the actual oil and gas well engineering, the present invention designed a simulation device for a casing/cement ring/formation combination of high-temperature and high-pressure oil and gas well. The present invention also calculates and determines device size and experimental testing and evaluating methods according to the working conditions of the oil and gas wells to be evaluated, thereby forming a seal integrity evaluation device and a method for high-temperature and high-pressure casing/cement ring/formation.

SUMMARY OF THE PRESENT INVENTION

Aiming at the deficiencies of the prior art, an object of the present invention is to provide a sealing integrity evaluation device for high-temperature and high-pressure casing cement ring formation and a method thereof, so as to solve the defects in the prior art.

Accordingly, in order to accomplish the above objects, the present invention provides:

a sealing integrity evaluation device for high-temperature and high-pressure casing cement ring formation, comprising: a high-temperature autoclave, a temperature and pressure control system, and a combination (12); wherein the high-temperature autoclave comprises: a kettle cover (1), a kettle body (2), an air inlet check valve (7), an air inlet pipeline (8), an air outlet pipeline (9), a bracket (11), and an exhaust valve (13), thereby realizing alternating high-temperature and high-pressure experimental conditions for sealing integrity evaluation of a casing/cement ring/formation combination;

the temperature and pressure control system comprises: a heating jacket (3), an insulation layer (4), a temperature and pressure probe (5), a temperature and pressure monitoring system (10), and a booster pump (6), thereby controlling temperatures and pressures as well as monitoring and recording experimental data during the sealing integrity evaluation of the casing/cement ring/formation combination;

the kettle cover (1) and the kettle body (2) together form a closed system through sealing; the air inlet pipeline (8) and the air outlet pipeline (9) are both connected to the closed system; the booster pump (6) is connected to the air inlet pipeline (8), and the air inlet check valve (7) is installed on the air inlet pipeline (8) to control air intake; the exhaust valve (13) is installed on the air outlet pipeline (9) to control exhaust; the bracket (11) is installed in the closed system to support the combination (12); during evaluation, the booster pump (6), the intake check valve (7) and the exhaust valve (13) can be used to increase or decrease a pressure of the high-temperature autoclave;

a surface of the kettle body (2) is covered by the heating jacket (3), and the heating jacket (3) is covered by the insulation layer (4); the temperature and pressure probe (5) penetrates the heating jacket (3), the insulation layer (4) and the kettle body (2); during the evaluation, the heating jacket (3) and the insulation layer (4) can be used to increase or decrease a temperature of the high-temperature autoclave, the temperature and pressure probe (5) can be used to monitor temperature and pressure changes in real time, and the temperature and pressure monitoring system (10) can be used to adjust internal temperature and pressure of the kettle body (2) in real time, so as to simulate alternating temperature and pressure conditions in the target well section of the high-temperature and high-pressure oil and gas well;

the combination (12) comprises: formation rock (14), the cement ring (15), the casing (16), a combination upper cover plate (17), a combination lower cover plate (18), a combination sealing ring (19), a casing sealing ring (20), combination upper cover handles (21), channel inspection pipelines (23), a channel inspection manifold (24), a casing valve (25), combination lower cover plugs (26), a casing cavity (27), combination lower cover handles (28), a straight joint (29), and steel wires, thereby simulating a full size or a compact size casing/cement ring/formation combination of a target well section of a high-temperature and high-pressure oil and gas well;

the combination (12) is a three-layer cylinder, which from inside to outside comprises the casing (16), the cement ring (15), and formation rock (14); the combination upper cover plate (17) is installed on an upper surface of the three-layer cylinder, and the combination lower cover plate (18) is installed on a lower surface of the three-layer cylinder; a first cementing interface is formed between the casing (16) and the cement ring (15), and a second cementing interface is formed between the cement ring (15) and the formation rock (14);

two combination upper cover handles (21) are symmetrically provided on the combination upper cover plate (17), and six combination upper cover plugs (22) are provided on a top portion of the combination upper cover plate (17); each of the combination upper cover plate plugs (22) is inserted with one of the channeling inspection pipelines (23); one ends of all the channel inspection pipelines (23) pass through the combination upper cover plugs (22) and the combination upper cover plate (17) and then enter the cement ring (15); the other ends of all the channel inspection pipelines (23) are converged to the channel inspection manifold (24) through the straight joint (29); one end of the straight joint (29) is connected to the channel inspection pipelines (23), and the other end of the straight joint (29) is connected to the channel inspection manifold (24); the channel inspection manifold (24) guarantees overall pressure testing;

an upper portion of the three-layer cylinder is sealed by the combination sealing ring (19), the combination upper cover plugs (22) and the casing sealing ring (20), and the channel inspection manifold (24) applies a channel inspection pressure to the cement ring (15); two combination lower cover handles (28) are symmetrically provided on the combination lower cover plate (18), and six combination lower cover plugs (26) and the casing valve (25) are provided on a surface of the combination lower cover plate (18); a lower portion of the three-layer cylinder is sealed by the combination sealing ring (19), the combination lower cover plugs (26) and the casing sealing ring (20), and is connected to a casing valve pipeline through the casing valve (25); the casing valve pipeline passes through the combination lower cover plate (18) and penetrates into the three-layer cylinder, thereby increasing or decreasing an internal pressure of the casing cavity (27); and the combination upper cover plugs (22) are connected to and sealed with the combination upper cover plate (17) by threads, and the combination lower cover plugs (26) are connected to and sealed with the combination lower cover plate (18) by threads, too; the combination upper cover handles (21) and the combination lower cover handles (28) are connected to the combination upper cover (17) and the combination lower cover (26) respectively through threads.

Preferably, the one ends of the six channel inspection pipelines (23) are bended to the first cementing interface or the second cementing interface according to evaluation requirements; a diameter of the channel inspection pipelines (23) is 3 mm, and a diameter of the steel wires inserted in the channel inspection pipelines (23) is 1 mm; one ends of the steel wires are fixed in the cement ring (15), and the other ends of the steel wires are fixed on the combination upper cover plate (17) through the combination upper cover plugs (22) and are then converged to the channel inspection manifold (24) through the straight joint (29); the steel wires are pulled out from the channel inspection pipelines (23) during channel inspection.

Preferably, the formation rock (14) is natural formation rock collected according to a wellbore size of the target well section of the high-temperature and high-pressure oil and gas well, or simulated rock processed according to a similarity principle; the cement ring (15) is formed by solidifying a cement slurry system used in the target well section of the high-temperature and high-pressure oil and gas well; the casing (16) is a full size casing used in the target well section of the high-temperature and high-pressure oil and gas well or a compact size casing designed according to the similarity principle.

Preferably, the kettle cover (1), the kettle body (2), the air inlet check valve (7), the air inlet pipeline (8), the air outlet pipeline (9) and the exhaust valve (13) are all made of Hastelloy C276;

the cement ring (15) is formed by solidifying the cement slurry system used in the target well section of the high-temperature and high-pressure oil and gas well;

a material of the casing (16) is identical to a casing material used in the target well section of the high-temperature and high-pressure oil and gas well;

materials of the combination upper cover plate (17), the combination lower cover plate (18), the combination upper cover handles (21), the combination upper cover plugs (22), and the combination lower cover plugs (26) are identical to the material of the casing (16);

the combination seal ring (19) and casing seal ring (20) are made of polytetrafluoroethylene; and the channel inspection pipelines (23), the channel inspection manifold (24), and the steel wires are made of the Hastelloy C276.

The present invention also provides a sealing integrity evaluation method for high-temperature and high-pressure casing cement ring formation, comprising steps of:

S1: according to a wellbore size, a casing size, and wellbore temperature and pressure condition parameters of a target well section of a high-temperature and high-pressure oil and gas well, choosing to use a full size or a compact size casing cement ring formation seal integrity evaluation device, wherein a full size refers to an evaluation device whose components are consistent with the target well section of the high-temperature and high-pressure oil and gas well in size parameters, and a compact size refers to a miniaturized evaluation device designed according to the size parameters of the target well section of the high-temperature and high-pressure oil and gas well using a similarity principle; then using the full size or calculating outer diameters, inner diameters and wall thicknesses of formation rock (14), a cement ring (15) and a casing (16) based on the similarity principle; determining a cement stone curing temperature, a curing pressure and a curing time, meanwhile determining internal pressures, confining pressures, environmental media, and channel inspection pressures of the casing (16) and the formation rock (14); setting a reasonable safety coefficient according to experimental conditions, and designing and processing the casing cement ring formation sealing integrity evaluation device;

S2: performing pressure tests on a high-temperature autoclave and a combination (12) to confirm qualified sealing for working conditions of the target well section of the high-temperature and high-pressure oil and gas well, and preparing cement slurry for the high-temperature and high-pressure oil and gas well to be evaluated;

S3: assembling the combination (12), and installing a combination upper cover (17), combination upper cover plugs (22) and channel inspection pipelines (23); wherein a diameter of the channel inspection pipelines (23) is 3 mm, and a diameter of steel wires inserted in the channel inspection pipelines (23) is 1 mm; a protruding length of an end of the steel wire is 3 mm, so as to pull the cement ring out after solidifying of the cement ring (15); pulling out is for channel inspection; after pulling out, gas can be injected to judge whether the cement ring is leaking according to whether the pressure is reduced or not; pulling out can prevent the cement slurry from from entering the channel inspection pipelines when it is not solidified; channel inspection is impossible if the channel inspection pipelines are blocked; then turning the combination (12) upside down, opening a combination lower cover (18), and pouring the prepared cement slurry continuously and smoothly into an annular space formed by the formation rock (14) and the casing (16); vibrating to eliminate air bubbles in the cement slurry, and then installing the combination lower cover plate (18) and combination lower cover plugs (26);

S4: opening a casing valve (25), and injecting water or nitrogen into the casing (16) until reaching the internal pressure determined in the step S1; then closing the casing valve (25) to maintain the internal pressure in a casing cavity (27) during evaluation;

S5: removing combination upper cover handles (21) and combination lower cover handles (28); putting the combination (12), which is filled with the cement slurry, into the high temperature autoclave; adding the environmental media determined in the step S1 into a kettle body (2), and curing under conditions comprising the curing temperature, the curing pressure and the curing time determined in the step S1, and an alternating temperature pressure; wherein during curing, temperature and pressure curves of the high-temperature autoclave are monitored in real time to ensure solidifying and curing conditions of the cement ring are consistent with the target well section of the high-temperature and high-pressure oil and gas well;

S6: after curing, taking out the combination (12), pulling out the steel wires inserted in the channel inspection pipelines (23), and connecting a channel inspection manifold (24) and a pressure gauge to the channel inspection pipelines (23) through a straight joint (29); removing the combination lower cover plugs (26), and immersing the combination (12) into water; pressurizing the channel inspection manifold (24) until reaching the channel inspection pressure determined in the step S1, and maintaining the pressure for 30 minutes; observing whether there are bubbles coming out, and recording pressure changes; inspecting the channel inspection pipelines (23) one by one to determine cementation conditions of a first cementing interface and a second cementing interface as well as a sealing ability of the cement ring;

S7: opening the combination (12), and intercepting a section from the channel inspection pipelines (23) to the combination lower cover plate (26); performing overall microscopic morphology and industrial CT analysis, and detecting defect morphologies and sizes comprising micro cracks and bubbles inside the cement ring;

S8: through intercepting samples on the cement ring (15), testing mechanical properties comprising compressive strength, tensile strength and triaxial compressive strength under comprehensive actions of the high temperature, the internal pressure, the confining pressure, and the media; and S9: combining channel inspection results under the comprehensive actions of the high temperature, the internal pressure, the confining pressure, and the media, the defect morphologies and sizes comprising the micro cracks and the bubbles inside the cement ring, and the mechanical properties comprising the compressive strength, the tensile strength and the triaxial compressive strength, thereby analyzing the cementation conditions of the first cementing interface and the second cementing interface and the sealing ability; and comprehensively analyzing and evaluating sealing integrity of the high-temperature and high-pressure oil and gas well casing/cement ring/formation combination under the comprehensive actions of the high temperature, the internal pressure, the confining pressure, and the media, so as to provide data support for cement slurry system formula optimization, performance improvement and cementing design of the high-temperature and high-pressure oil and gas well.

Compared with the prior art, the present invention has advantages as follows.

(A) The present invention is able to design and process the full-size or the compact-size casing cement ring formation seal integrity evaluation device according to the wellbore size, the casing size and the working condition parameters of the target well section of the high-temperature and high-pressure oil and gas well, thereby performing evaluation experiments.

(B) Under the environmental conditions of alternating temperatures, alternating pressures and alternating internal pressures, the present invention is able to evaluate casing/cement ring/formation combination leakage, internal defect morphology and size, and mechanical property changes such as compressive strength, tensile strength and triaxial compression strength.

(C) The present invention is close to engineering practice of the high-temperature and high-pressure oil and gas well, and can detect the cementation conditions of the first cementing interface and the second cementing interface and the sealing ability, thereby analyzing and evaluating sealing integrity of the high-temperature and high-pressure oil and gas well casing/cement ring/formation combination under the comprehensive actions of the high temperature, the internal pressure, the confining pressure, and the media, so as to provide more stable and reliable experimental methods and data support for cement slurry system optimization, formula design and performance improvement of the high-temperature and high-pressure oil and gas well.

DETAILED DESCRIPTION OF THE PREFERRED EMBODIMENT

In order to make the objects, technical solutions, and advantages of the present invention clearer, the present invention will be further described below with reference to the accompanying drawings and embodiments.

Figure 1:
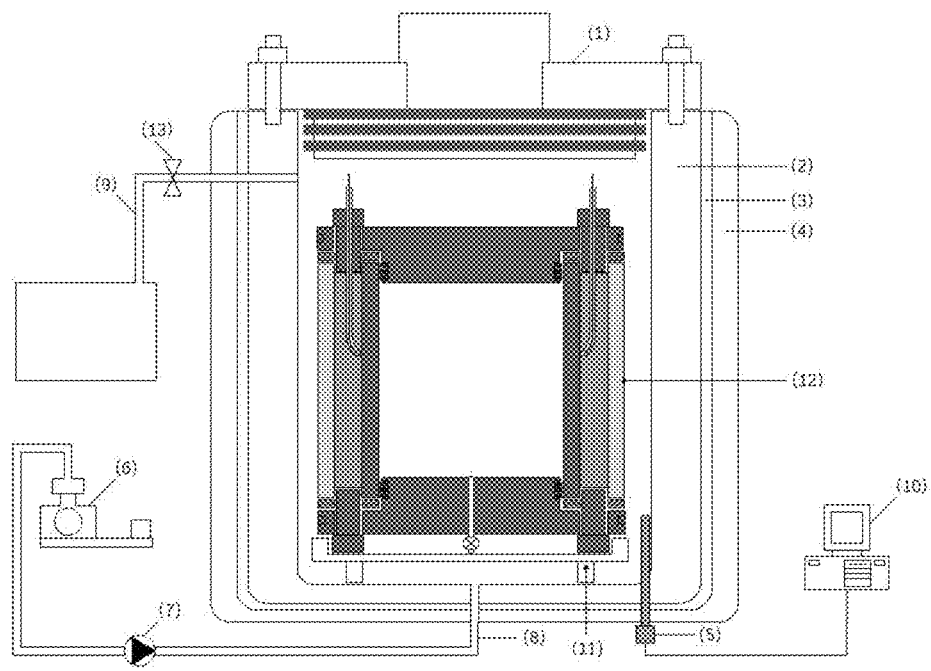
FIG. 1 is a structural view of a sealing integrity evaluation device for high-temperature and high-pressure casing cement ring formation according to an embodiment of the present invention.
Figure 2:
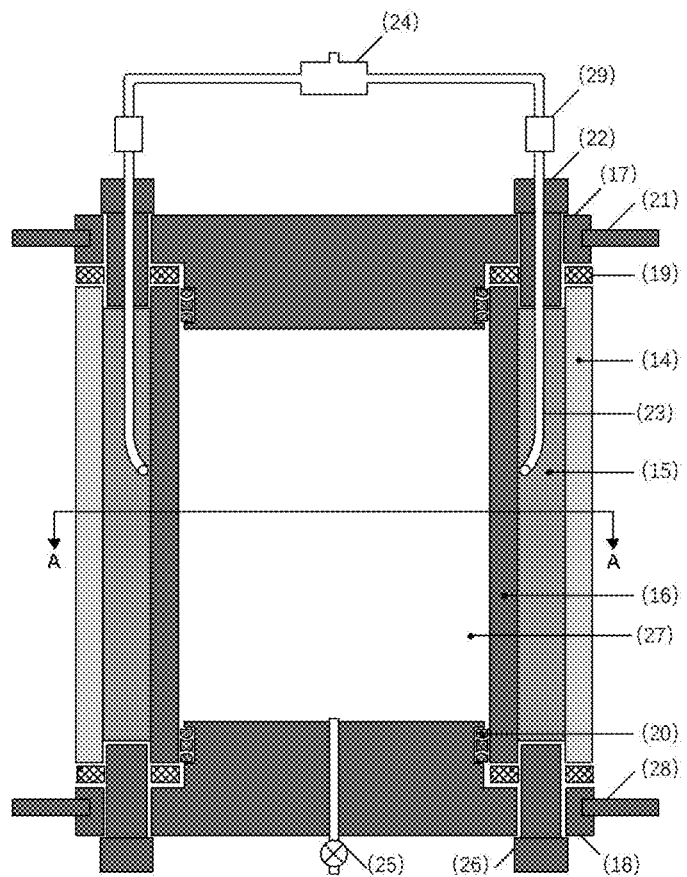
FIG. 2 is a sketch view of a casing cement ring formation combination according to the embodiment of the present invention.
Figure 3:
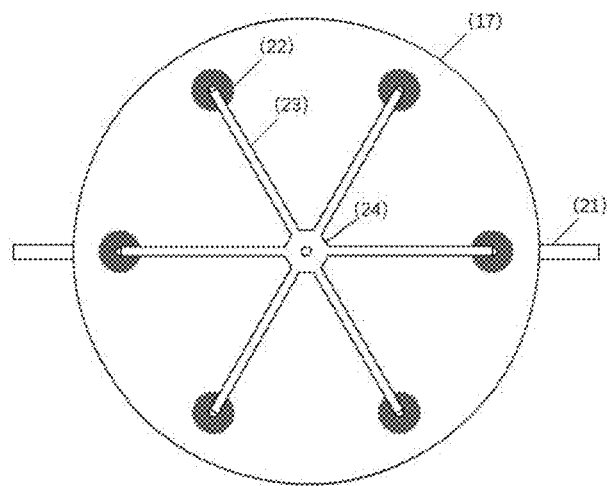
FIG. 3 is a sketch view of a combination upper cover plate of the casing cement ring formation combination according to the embodiment of the present invention.
Figure 4:
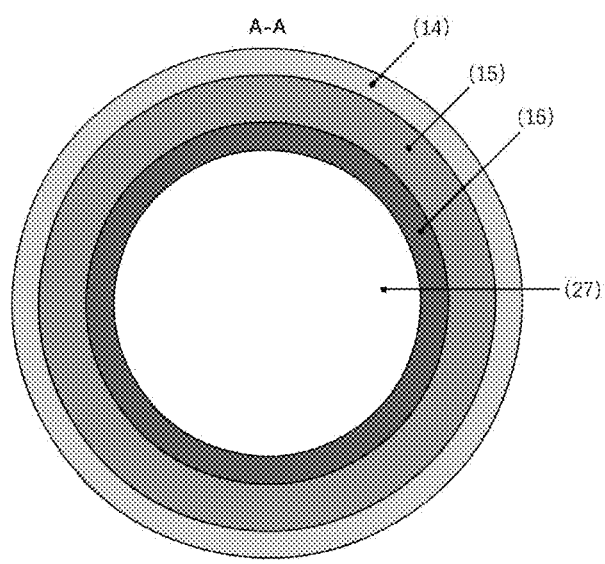
FIG. 4 is an A-A cross-sectional view of the casing cement ring formation combination according to the embodiment of the present invention.
Figure 5:
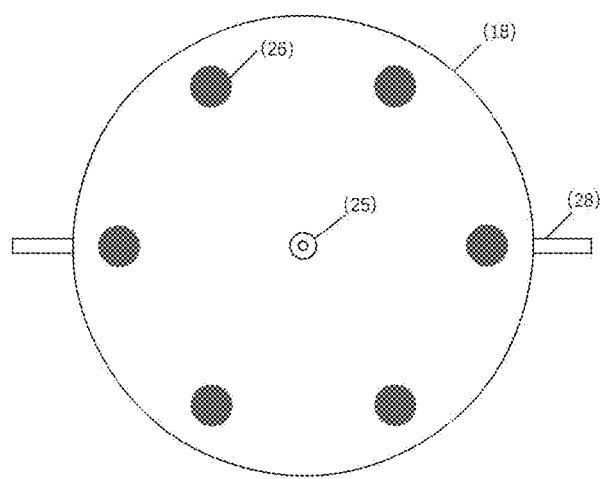
FIG. 5 is a sketch view of a combination lower cover plate of the casing cement ring formation combination according to the embodiment of the present invention.

Referring to FIG. 1, a sealing integrity evaluation device for high-temperature and high-pressure casing cement ring formation, comprising: a high-temperature autoclave, a temperature and pressure control system, and a simulated casing/cement ring/formation combination. The present invention can simulate and evaluate sealing integrity of the casing/cement ring/formation combination under high temperature, internal pressure, confining pressure, and their alternating effects.

The high-temperature autoclave comprises: a kettle cover 1, a kettle body 2, an air inlet check valve 7, an air inlet pipeline 8, an air outlet pipeline 9, a bracket 11, and an exhaust valve 13, thereby realizing alternating high-temperature and high-pressure experimental conditions for sealing integrity evaluation of a casing/cement ring/formation combination.

The temperature and pressure control system comprises: a heating jacket 3, an insulation layer 4, a temperature and pressure probe 5, a temperature and pressure monitoring system 10, and a booster pump 6, thereby controlling temperatures and pressures as well as monitoring and recording experimental data during the sealing integrity evaluation of the casing/cement ring/formation combination.

The kettle cover 1 and the kettle body 2 together form a closed system through sealing; the air inlet pipeline 8 and the air outlet pipeline 9 are both connected to the closed system; the booster pump 6 is connected to the air inlet pipeline 8, and the air inlet check valve 7 is installed on the air inlet pipeline 8; the exhaust valve 13 is installed on the air outlet pipeline 9; the bracket 11 is installed in the closed system, and the simulated casing/cement ring/formation combination is installed on the bracket 11; during evaluation, the booster pump 6, the intake check valve 7 and the air inlet pipeline 8 can be used to increase or decrease a pressure of the high-temperature autoclave.

A surface of the kettle body 2 is covered by the heating jacket 3, and the heating jacket 3 is covered by the insulation layer 4; the temperature and pressure probe 5 penetrates the heating jacket 3, the insulation layer 4 and the kettle body 2; during the evaluation, the heating jacket 3 and the insulation layer 4 can be used to increase or decrease a temperature of the high-temperature autoclave, the temperature and pressure probe 5 can be used to monitor temperature and pressure changes in real time, and the temperature and pressure monitoring system 10 can be used to adjust internal temperature and pressure of the kettle body 2 in real time, so as to simulate alternating temperature and pressure conditions in the target well section of the high-temperature and high-pressure oil and gas well.

Referring to FIGS. 2-5, the combination 12 comprises: formation rock 14, the cement ring 15, the casing 16, a combination upper cover plate 17, a combination lower cover plate 18, a combination sealing ring 19, a casing sealing ring 20, combination upper cover handles 21, combination upper cover plugs 22, channel inspection pipelines 23, a channel inspection manifold 24, a casing valve 25, combination lower cover plugs 26, a casing cavity 27, combination lower cover handles 28, a straight joint 29, and steel wires, thereby simulating a full size or a compact size casing/cement ring/formation combination of a target well section of a high-temperature and high-pressure oil and gas well.

The casing 16 is covered by the cement ring 15, and the cement ring 15 is covered by the formation rock 14 to form a tube-like three-layer cylinder; the combination upper cover plate 17 is installed on an upper surface of the three-layer cylinder, and the combination lower cover plate 18 is installed on a lower surface of the three-layer cylinder; a first cementing interface is formed between the casing 16 and the cement ring 15, and a second cementing interface is formed between the cement ring 15 and the formation rock 14.

Two combination upper cover handles 21 are symmetrically provided on the combination upper cover plate 17, and six combination upper cover plugs 22 are provided on a top portion of the combination upper cover plate 17; each of the combination upper cover plate plugs 2 is inserted with one of the channeling inspection pipelines 23; one ends of all the channel inspection pipelines 23 pass through the combination upper cover plugs 22 and the combination upper cover plate 17 and then enter the cement ring 15; the other ends of all the channel inspection pipelines 23 are converged to the channel inspection manifold 24.

An upper portion of the three-layer cylinder is sealed by the combination sealing ring 19, the combination upper cover plugs 22 and the casing sealing ring 20, and the channel inspection manifold 24 applies a channel inspection pressure to the cement ring 15.

Two combination lower cover handles 28 are symmetrically provided on the combination lower cover plate 18, and six combination lower cover plugs 26 and the casing valve 25 are provided on a surface of the combination lower cover plate 18; a lower portion of the three-layer cylinder is sealed by the combination sealing ring 19, the combination lower cover plugs 26 and the casing sealing ring 20, and is connected to a casing valve pipeline through the casing valve 25; the casing valve pipeline passes through the combination lower cover plate 18 and penetrates into the three-layer cylinder, thereby increasing or decreasing an internal pressure of the casing cavity 27.

The combination upper cover plugs 22 are connected to and sealed with the combination upper cover plate 17 by threads, and the combination lower cover plugs 26 are connected to and sealed with the combination lower cover plate 18 by threads, too; the combination upper cover handles 21 and the combination lower cover handles 28 are connected to the combination upper cover 17 and the combination lower cover 26 respectively through threads.

The one ends of the six channel inspection pipelines 23 are bended to the first cementing interface or the second cementing interface according to evaluation requirements, and the steel wires are inserted in the channel inspection pipelines 23; the steel wires can be pulled out during channel inspection; one ends of the steel wires are fixed in the cement ring 15, and the other ends of the steel wires are fixed on the combination upper cover plate 17 through the combination upper cover plugs 22 and are then converged to the channel inspection manifold 24 through the straight joint 29; the steel wires are pulled out from the channel inspection pipelines 23 during channel inspection.

There are a full size and a compact size wellbore for the target well section of the high-temperature and high-pressure oil and gas well, wherein a full size refers to an evaluation device whose components are consistent with the target well section of the high-temperature and high-pressure oil and gas well in size parameters, and a compact size refers to a miniaturized evaluation device designed according to the size parameters of the target well section of the high-temperature and high-pressure oil and gas well using a similarity principle; the formation rock 14 is natural formation rock collected according to a wellbore size of the target well section of the high-temperature and high-pressure oil and gas well, or simulated rock processed according to a similarity principle; the cement ring 15 is formed by solidifying a cement slurry system used in the target well section of the high-temperature and high-pressure oil and gas well; the casing 16 is a full size casing used in the target well section of the high-temperature and high-pressure oil and gas well or a compact size casing designed according to the similarity principle.

The combination 12 is heated by the heating jacket 3. The confining pressure of the combination 12 is increased by the booster pump 6, and the internal pressure of the combination 12 is increased by the casing valve 25. The temperature and pressure of the kettle body 2 are controlled to simulate solidification of the cement ring of the target well section under high-temperature and high-pressure conditions. At the same time, the channel inspection pipelines 23 are solidified in the cement ring 15 through the combination upper cover plugs 22. According to the evaluation, the ends of the channel inspection pipelines 23 are appropriately bended to the first cementing interface or the second cementing interface. After solidifying of the cement, the channel inspection pipelines 23 are inspected one by one to determine cementation conditions of a first cementing interface and a second cementing interface as well as a sealing ability of the cement ring. Cracks, bubbles, defect morphologies and sizes of the cement ring 15 are analyzed through microscopic morphology and industrial CT. Through intercepting samples on the cement ring 15, mechanical properties are tested, comprising compressive strength, tensile strength and triaxial compressive strength under comprehensive actions of the high temperature, the internal pressure, the confining pressure, and the media, so as to simulate and evaluate the sealing integrity of the casing/cement ring/formation combination of the target well section of the high-temperature and high-pressure oil and gas well, and to screen the cement slurry system or optimize cement slurry formula.

The kettle cover 1, the kettle body 2, the air inlet check valve 7, the air inlet pipeline 8, the air outlet pipeline 9 and the exhaust valve 13 are all made of Hastelloy C276; the formation rock 14 is formation rock collected from the target well section of the high-temperature and high-pressure well, or simulated rock with the same rock mechanics properties; the cement ring 15 is formed by solidifying the cement slurry system used in the target well section of the high-temperature and high-pressure oil and gas well; a material of the casing 16 is identical to a casing material used in the target well section of the high-temperature and high-pressure oil and gas well; materials of the combination upper cover plate 17, the combination lower cover plate 18, the combination upper cover handles 21, the combination upper cover plugs 22, and the combination lower cover plugs 26 are identical to the material of the casing 16; the combination seal ring 19 and casing seal ring 20 are made of polytetrafluoroethylene; and the channel inspection pipelines 23, the channel inspection manifold 24, and the steel wires are made of the Hastelloy C276.

The present invention also provides a sealing integrity evaluation method for high-temperature and high-pressure casing cement ring formation, comprising steps of:

S1: processing a sealing integrity evaluation device for high-temperature and high-pressure casing cement ring formation, which specifically comprising steps of:

S11: according to a wellbore size, a casing size, and wellbore temperature and pressure condition parameters of a target well section of a high-temperature and high-pressure oil and gas well, choosing to use a full size or a compact size casing cement ring formation seal integrity evaluation device; then using the full size or calculating outer diameters, inner diameters and wall thicknesses of formation rock 14, a cement ring 15 and a casing 16 based on the similarity principle, wherein:

an actual wellbore size p and a simulation device size m are recorded as data sets $p_n$ and $m_n$; 7 key geometric dimensions involved are a casing outer diameter A, a casing inner diameter B, a casing wall thickness C, a cement ring outer diameter D, a cement ring inner diameter E, a cement ring wall thickness F, and a borehole size G; then the actual size of the wellbore and the size of the simulation device are expressed as:

$$p_n = (p_A, p_B, p_C, p_D, p_E, p_F, p_G)$$

$$m_n = (m_A, m_B, m_C, m_D, m_E, m_F, m_G)$$

according to a Euclidian distance method, standard deviations $S_n$ of the actual wellbore size p and the simulation device size m are calculated:

$$p_n^* = \frac{p_n - \bar{p}}{s}, m_n^* = \frac{m_n - \bar{m}}{s}$$

wherein $p_n^x$ and $m_n^y$ are standardized variables of the actual size of the wellbore p and the size of the simulation device m; $\bar{p}$ and $\bar{m}$ are mean values of corresponding size parameters of the actual wellbore size p and the simulation device size m; $s_n$ is a standard deviation of the corresponding size parameters;

the Euclidian distance between the actual wellbore size p and the simulation device size m is:

$$E(p, m) = \sqrt{\sum_{n=1}^{7}\left(\frac{p_n - m_n}{s_n}\right)^2} = \sqrt{(p_1 - m_1)^2 + (p_2 - m_2)^2 + \ldots + (p_7 - m_7)^2}$$

the size of the simulation device is design according to the above method; when the calculated Euclidean distance between the actual wellbore size p and the simulation device size m is $E(p, m) \in [0,1]$, it is indicated that the actual wellbore size p and the simulation device size m satisfy similarity design requirements;

S12: according to the working conditions of the target well section of the high-temperature and high-pressure oil and gas well, determining a cement stone curing temperature, a curing pressure and a curing time, meanwhile determining internal pressures, confining pressures, environmental media, and channel inspection pressures of the casing 16 and the formation rock 14;

S13: according to the above-mentioned full-size or compact size casing/cement ring/formation combination size and temperature, pressure and media requirements for material, setting a reasonable safety coefficient according to experimental conditions, and designing and processing the casing cement ring formation sealing integrity evaluation device; and S14: performing pressure tests on a high-temperature autoclave and a combination 12 to confirm device performances and qualified sealing for working conditions of the target well section of the high-temperature and high-pressure oil and gas well, and preparing cement slurry for the high-temperature and high-pressure oil and gas well to be evaluated;

S2: preparing the casing cement ring formation combination, which specifically comprises steps of:

S21: preparing cement slurry for the high-temperature and high-pressure oil and gas well to be evaluated;

S22: assembling the combination 12, and installing a combination upper cover 17, combination upper cover plugs 22, the combination sealing ring 19, the casing sealing ring 20, and channel inspection pipelines 23; appropriately bending the ends of the channel inspection pipelines 23 to the first cementing interface or the second cementing interface according to evaluation requirement, so as to determine cementation conditions of a first cementing interface and a second cementing interface as well as a sealing ability after solidifying; inserting the steel wires with a corresponding size into the channel inspection pipelines 23, and leaving a certain length at one ends to facilitate pulling out when curing is completed; and then turning the combination 12 upside down; and S23: pouring the cement slurry prepared in the step S21 continuously and smoothly into an annular space of the combination 12; vibrating to eliminate air bubbles in the cement slurry, and then installing the combination lower cover plate 18, the combination lower cover plugs 26, the combination sealing ring 19, the casing sealing ring 20, and the casing valve 25;

S3: applying internal pressures, which specifically comprising steps of:

S31: connecting the booster pump to the combination lower cover plate 18 of the casing/cement ring/formation combination;

S32: opening a casing valve 25, and increasing the pressure of the casing 16 until reaching the internal pressure of the casing cavity reaches the internal pressure determined in the step S1; and S33: closing the casing valve 25 and disconnecting the booster pump and the combination lower cover plate 18 of the casing/cement ring/formation combination, so as to maintain the internal pressure in a casing cavity 27 during evaluation;

S4: applying comprehensive actions of alternating high temperatures, internal pressures, confining pressures, and media on the casing cement ring formation combination, which specifically comprises steps of:

S41: slowly and smoothly putting the combination 12 into the kettle body 2 of the high-temperature autoclave; adding the environmental media determined in the step S1 into a kettle body 2, and installing the kettle cover for sealing;

S42: increasing temperature and pressure until the temperature and pressure of the kettle body 2 of the high-temperature autoclave reaches the curing temperature and the curing pressure determined in the step S1; and recording an experiment starting time;

S43: during curing, using the temperature and pressure control system to adjust and monitor changes in temperature and pressure of the high-temperature autoclave, wherein the alternating temperature and pressure and the cement curing time are determined in the S1; and S44: after curing, taking out the combination 12 from the high-temperature autoclave and preparing for subsequent experiments;

S5: performing channel inspection to the casing cement ring formation combination under the comprehensive actions of the high temperature, the internal pressure, the confining pressure, and the media, which specifically comprises steps of:

S51: after curing, taking out the combination 12 from the high-temperature autoclave, and pulling out the steel wires from the channel inspection pipelines 23;

S52: connecting a channel inspection manifold 24 and a pressure gauge to the channel inspection pipelines 23 through a straight joint 29; removing the combination lower cover plugs 26, and immersing the combination 12 into water; and S53: pressurizing the channel inspection manifold 24 until reaching the channel inspection pressure determined in the step S1, and maintaining the pressure for 30 minutes; observing whether there are bubbles coming out; inspecting and recording pressure changes of the channel inspection pipelines 23 one by one in a clockwise direction, so as to determine cementation conditions of a first cementing interface and a second cementing interface as well as a sealing ability of the cement ring;

S6: observing a microstructure of the cement ring in casing cement ring formation combination under the comprehensive actions of the high temperature, the internal pressure, the confining pressure, and the media, which specifically comprises steps of:

S61: opening the combination 12, and intercepting a section from the channel inspection pipelines 23 to the combination lower cover plate 26; performing overall industrial CT scanning;

S62: detecting defect morphologies and sizes comprising micro cracks and bubbles inside the cement ring; and S63: analyzing the cementation condition of the first cementing interface between the casing and the cement ring, and the cementation condition of the second cementing interface between the cement ring and the formation rock, and sealing abilities of the first and second cementing interfaces;

S7: testing mechanical properties of the cement ring in the casing cement ring formation combination under the comprehensive actions of the high temperature, the internal pressure, the confining pressure, and the media, which specifically comprises steps of:

S71: opening the combination 12, and intercepting test samples between the channel inspection pipelines 23 and the combination lower cover plugs 26 for testing uniaxial compressive strength, tensile strength, and triaxial compressive strength; wherein the uniaxial compressive strength test sample and the triaxial compressive strength test sample are cylindrical samples with a diameter of 25.4 mm and a height of 50.8 mm, and the tensile strength test samples are cylindrical samples with a diameter of 50.8 mm and a height of 25.4 mm;

S72: testing mechanical properties comprising compressive strength, tensile strength and triaxial compressive strength under the comprehensive actions of the high temperature, the internal pressure, the confining pressure, and the media; wherein:

compressive strength:

$$R = \frac{P}{S}$$

wherein P is a maximum force to break the cement stone sample, and S is a minimum cross-sectional area;

tensile strength:

$$\sigma_t = \frac{2P}{\pi Dt}$$

wherein P is a load when the sample is broken, MPa; D is a height of a cube sample or a diameter of a cylindrical sample, mm; t is a width of the cube sample or a thickness of the cylindrical sample, mm; and S73: by comparing mechanical property changes of the cement ring before and after the comprehensive actions of the high temperature, the internal pressure, the confining pressure, and the media, obtaining an ability of the cement ring to withstand the high temperature, the internal pressure, the confining pressure, and the media, and obtaining mechanical property change laws under such working environment; and S8: combining channel inspection results under the comprehensive actions of the high temperature, the internal pressure, the confining pressure, and the media, the defect morphologies and sizes comprising the micro cracks and the bubbles inside the cement ring, and the mechanical properties comprising the compressive strength, the tensile strength and the triaxial compressive strength; and comprehensively analyzing and evaluating sealing integrity of the high-temperature and high-pressure oil and gas well casing/cement ring/formation combination under the comprehensive actions of the high temperature, the internal pressure, the confining pressure, and the media, so as to provide data support for cement slurry system formula optimization, performance improvement and cementing design of the high-temperature and high-pressure oil and gas well.

Those skilled in the art will realize that the above embodiment helps the readers understand the implementation of the present invention, but the protection scope of the present invention is not limited to such specific description and embodiment. Also, based on the embodiment of the present invention, those skilled in the art can make various modifications and combinations without departing from the essence of the present invention, and these modifications and combinations still fall within the protection scope of the present invention.

What is claimed is:

1. A sealing integrity evaluation device for casing cement ring formation, comprising: an autoclave, a temperature and pressure control system, and a three-layer cylinder (12); wherein the autoclave comprises: a kettle cover (1), a kettle body (2), an air inlet check valve (7), an air inlet pipeline (8), an air outlet pipeline (9), a bracket (11), and an exhaust valve (13), thereby realizing alternating temperature and pressure conditions for sealing integrity evaluation of a casing/cement ring/formation combination;

the temperature and pressure control system comprises: a heating jacket (3), an insulation layer (4), a temperature and pressure probe (5), a temperature and pressure monitoring system (10), and a booster pump (6), thereby controlling temperatures and pressures as well as monitoring and recording data during the sealing integrity evaluation of the casing/cement ring/formation combination;

the kettle cover (1) and the kettle body (2) together form a closed system through sealing; the air inlet pipeline (8) and the air outlet pipeline (9) are both connected to the closed system; the booster pump (6) is connected to the air inlet pipeline (8), and the air inlet check valve (7) is installed on the air inlet pipeline (8) to control air intake; the exhaust valve (13) is installed on the air outlet pipeline (9) to control exhaust; the bracket (11) is installed in the closed system to support the three-layer cylinder (12);

a surface of the kettle body (2) is covered by the heating jacket (3), and the heating jacket (3) is covered by the insulation layer (4); the temperature and pressure probe (5) penetrates the heating jacket (3), the insulation layer (4) and the kettle body (2);

the three-layer cylinder (12) comprises: formation rock (14), the cement ring (15), the casing (16), a combination upper cover plate (17), a combination lower cover plate (18), a combination sealing ring (19), a casing sealing ring (20), combination upper cover handles (21), combination upper cover plugs (22), channel inspection pipelines (23), a channel inspection manifold (24), a casing valve (25), combination lower cover plugs (26), a casing cavity (27), combination lower cover handles (28), a straight joint (29), and steel wires;

the (12) three-layer cylinder, from inside to outside, comprises the casing (16), the cement ring (15), and formation rock (14); the combination upper cover plate (17) is installed on an upper surface of the three-layer cylinder, and the combination lower cover plate (18) is installed on a lower surface of the three-layer cylinder; a first cementing interface is formed between the casing (16) and the cement ring (15), and a second cementing interface is formed between the cement ring (15) and the formation rock (14);

two combination upper cover handles (21) are symmetrically provided on the combination upper cover plate (17), and six combination upper cover plugs (22) are provided on a top portion of the combination upper cover plate (17); each of the combination upper cover plate plugs (2) is inserted with one of the channeling inspection pipelines (23); one ends of all the channel inspection pipelines (23) pass through the combination upper cover plugs (22) and the combination upper cover plate (17) and then enter the cement ring (15); the other ends of all the channel inspection pipelines (23) are converged to the channel inspection manifold (24) through the straight joint (29); one end of the straight joint (29) is connected to the channel inspection pipelines (23), and the other end of the straight joint (29) is connected to the channel inspection manifold (24);

an upper portion of the three-layer cylinder is sealed by the combination sealing ring (19), the combination upper cover plugs (22) and the casing sealing ring (20), and the channel inspection manifold (24) applies a channel inspection pressure to the cement ring (15); two combination lower cover handles (28) are symmetrically provided on the combination lower cover plate (18), and six combination lower cover plugs (26) and the casing valve (25) are provided on a surface of the combination lower cover plate (18); a lower portion of the three-layer cylinder is sealed by the combination sealing ring (19), the combination lower cover plugs (26) and the casing sealing ring (20), and is connected to a casing valve pipeline through the casing valve (25); the casing valve pipeline passes through the combination lower cover plate (18) and penetrates into the three-layer cylinder, thereby increasing or decreasing an internal pressure of the casing cavity (27); and the combination upper cover plugs (22) are connected to and sealed with the combination upper cover plate (17) by threads, and the combination lower cover plugs (26) are connected to and sealed with the combination lower cover plate (18) by threads, too; the combination upper cover handles (21) and the combination lower cover handles (28) are connected to the combination upper cover (17) and the combination lower cover (26) respectively through threads.

2. The sealing integrity evaluation device, as recited in claim 1, wherein the one ends of the six channel inspection pipelines (23) are vertically inserted into the cement ring, and are bent to the first cementing interface or the second cementing interface; a diameter of the channel inspection pipelines (23) is 3 mm, and a diameter of the steel wires inserted in the channel inspection pipelines (23) is 1 mm; one ends of the steel wires are fixed in the cement ring (15), and the other ends of the steel wires are fixed on the combination upper cover plate (17) through the combination upper cover plugs (22) and are then converged to the channel inspection manifold (24) through the straight joint (29); the steel wires are pulled out from the channel inspection pipelines (23) during channel inspection.

3. The sealing integrity evaluation device, as recited in claim 2, wherein the formation rock (14) is natural formation rock collected according to a wellbore size of a target well section of the oil and gas well.

4. The sealing integrity evaluation device, as recited in claim 3, wherein the kettle cover (1), the kettle body (2), the air inlet check valve (7), the air inlet pipeline (8), the air outlet pipeline (9) and the exhaust valve (13) are all made of Hastelloy C276;

the cement ring (15) is formed by solidifying a cement slurry used in the target well section of the oil and gas well;

a material of the casing (16) is identical to a casing material used in the target well section of the oil and gas well;

materials of the combination upper cover plate (17), the combination lower cover plate (18), the combination upper cover handles (21), the combination upper cover plugs (22), and the combination lower cover plugs (26) are identical to the material of the casing (16);

the combination seal ring (19) and casing seal ring (20) are made of polytetrafluoroethylene; and the channel inspection pipelines (23), the channel inspection manifold (24), and the steel wires are made of the Hastelloy C276.

* * * * *